US012544323B2

(12) United States Patent
Borgnini

(10) Patent No.: US 12,544,323 B2
(45) Date of Patent: Feb. 10, 2026

(54) HAIR PROTECTION AND RESTRUCTURING METHOD AND THE RELATED COMPOSITIONS

(71) Applicant: BEAUTY & BUSINESS S.p.A., Milan (IT)

(72) Inventor: Gianluca Borgnini, Carvico (IT)

(73) Assignee: BEAUTY & BUSINESS S.p.A., Milan (IT)

( * ) Notice: Subject to any disclaimer, the term of this patent is extended or adjusted under 35 U.S.C. 154(b) by 273 days.

(21) Appl. No.: 18/484,519

(22) Filed: Oct. 11, 2023

(65) Prior Publication Data

US 2024/0122830 A1 Apr. 18, 2024

(30) Foreign Application Priority Data

Oct. 12, 2022 (IT) ........................ 102022000021039

(51) Int. Cl.

| | |
|---|---|
| ***A61K 8/365*** | (2006.01) |
| ***A61K 8/49*** | (2006.01) |
| ***A61Q 5/08*** | (2006.01) |

(52) U.S. Cl.

CPC ............ *A61K 8/365* (2013.01); *A61K 8/4913* (2013.01); *A61Q 5/08* (2013.01); *A61K 2800/884* (2013.01)

(58) Field of Classification Search

CPC .................. A61K 8/365; A61K 8/4913; A61K 2800/884; A61K 8/27; A61Q 5/08; A61Q 5/002

See application file for complete search history.

(56) References Cited

FOREIGN PATENT DOCUMENTS

JP 2020011905 A 1/2020

OTHER PUBLICATIONS

Search Report of priority application IT 102022000021039 issued Apr. 20, 2023.

*Primary Examiner* — Jessica Worsham

(74) *Attorney, Agent, or Firm* — Silvia Salvadori, P.C.; Silvia Salvadori

(57) ABSTRACT

The subject of the invention is a hair protection and restructuring method comprising the application, before dyeing/bleaching treatments, of a first composition at pH 7.0-9.5 comprising levulinic acid, and a post-treatment, following dyeing/bleaching, with a composition at pH 3.5-4.5 comprising the zinc salt of pyrrolidone carboxylic acid.

7 Claims, 4 Drawing Sheets

HAIR PROTECTION AND RESTRUCTURING METHOD AND THE RELATED COMPOSITIONS

This application claims priority to and the benefit of Italian Patent Application No. 102022000021039, filed Oct. 20, 2022, the contents of which is incorporated herein by reference in its entirety.

The subject of the invention is a hair protection and restructuring method comprising the application, before dyeing/bleaching treatments, of a first composition at pH 7.0-9.5 comprising levulinic acid, and a post-treatment, following dyeing/bleaching, with a composition at pH 3.5-4.5 comprising the zinc salt of pyrrolidone carboxylic acid.

PRIOR ART

Cosmetic hair treatments such as bleaching and permanent dyeing often damage the hair structure. Following said treatments, especially if repeated, the hair tends to become fragile and unmanageable, easily breaks, and is hard to comb. The damage thus caused makes the result of successive dyeing and bleaching operations increasingly unsatisfactory in terms of uniformity of colour and resistance to washing.

The hair structure is formed by alpha-keratin chains. The strength of the hair is provided by said polypeptide keratin helices oriented parallel to the longitudinal axis of the hair fibre. The helical structure is stabilised by hydrogen bonds, ionic, hydrophobic and coulombian interactions, and covalent bonds such as disulphide bridges.

The greater the density of said bonds, the stronger the hair.

There is consequently a real need to preserve and improve the quality of the fibre, optimising the bond density between the proteins to guarantee the strength and cosmetic properties of the hair, during dyeing and bleaching treatments.

There is also a need to guarantee that repeated applications of cosmetic dye always perform equally well.

In the last 10 years various patents have been filed relating to methods and compositions designed to protect the bonds in the capillary fibre during the most aggressive cosmetic treatments.

WO2017091794 relates to the use of a composition based on monoethanolamine and at least one dicarboxylic acid, in particular maleic acid.

WO2018191362 relates to the use of at least one dicarboxylic acid, including maleic acid. WO2019198114 relates to the use of a composition based on maleic acid and liposol maleate.

Malic and maleic dicarboxylic acids form crosslinked amide bonds. Numerous maleic/malic acid-based products already on the market are claimed to protect the bonds in the capillary fibre against aggressive cosmetic treatments.

Said products are kits consisting of two compositions, one of which is designed to be mixed with the cosmetic bleaching/dyeing treatment to protect the bonds in the hair, while the other is applied at the end of the treatment to seal the cuticles.

The products designed to be mixed with the cosmetic treatment usually have a pH of 3-4 that alters the pH of the bleaching/dyeing treatment (which is between 9 and 11), as stated in WO2018191362.

However, adding a composition to the bleach or dye, even at a compatible pH, would lead to dilution of the active ingredients and a possible interaction with them, which could alter the result. JP2020011905 describes a leave-on pre-treatment based on citric acid and/or levulinic acid and/or maleic acid designed to protect the hair when permanent dyes or bleaches are used. The compositions described have a pH of 5 or lower, and under such conditions it is known that the cuticles are closed and therefore less receptive to the subsequent treatment, leading to a dyeing/bleaching result which is unsatisfactory in terms of depth and evenness.

There is consequently a need for a method that effectively protects the hair by preserving the bond density during aggressive cosmetic treatments without interfering in any way with the treatment, but improving its quality and efficacy.

The present invention therefore offers a method of preserving bond density in the hair during a dyeing/bleaching treatment, at the same time improving the performance of said treatment.

DESCRIPTION OF THE INVENTION

Figure 1:
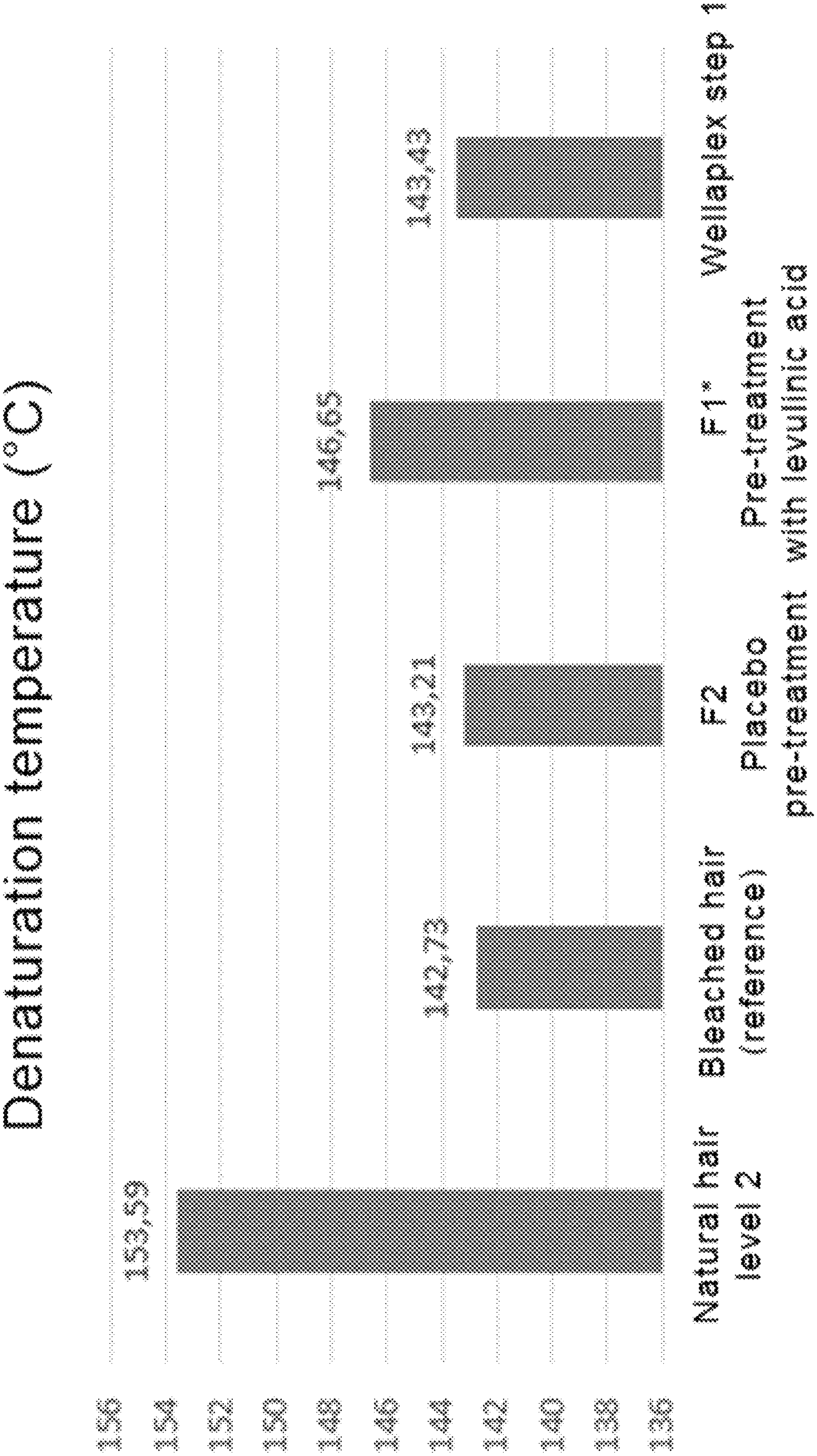
FIG. 1 shows the mean denaturation temperatures TD measured from the various samples.

It has been found that a composition containing levulinic acid in percentages ranging from 0.5 to 2.5% of the weight of the composition, and having a pH ranging from 7.0 to 9.5, if applied in leave-in form to the hair before dyeing/bleaching, effectively protects the integrity of the hair bonds, promoting a more uniform result. The application of a post-treatment at pH 3.5-4.5 containing zinc PCA (pyrrolidone carboxylic acid zinc salt) at a percentage ranging from 0.01 to 0.5% by weight of the composition completes the treatment, restoring the bond density of natural hair, ie. hair which has not undergone any treatment, and the cosmetic properties of the hair.

The compositions can take the form of an O/W (oil-in-water) or W/O (water-in-oil) emulsion, an aqueous solution, biphasic liquid, gel, oil, aerosol or mousse, or can be in solid form. The compositions can also contain one or more additives commonly used in the cosmetic industry such as solvents, emulsifiers, wetting agents, surfactants, thickeners, conditioning agents and auxiliaries.

Examples of solvents include water, low-molecular-weight aliphatic mono- or polyalcohols and esters and ethers thereof, in particular alkanols having 1 to 4 carbon atoms, such as ethanol, n-propanol, isopropanol, butanol and isobutanol; bivalent or trivalent alcohols, in particular having 2 to 6 carbon atoms, such as ethylene glycol, propylene glycol, 1,3-propanediol, 1, 4-butanediol, 1,5-pentanediol, 1,6-hexanediol, 1,2,6-hexanetriol, glycerin, diethylene glycol, dipropylene glycol and polyalkylene glycols such as triethylene glycol, polyethylene glycol, tripropylene glycol and polypropylene glycol; low-molecular-weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular having 3 to 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropylether; esters such as ethyl formate, methyl formate, methyl acetate, ethyl acetate, propyl acetate, butyl acetate, phenyl acetate, ethylene glycol monoethyl ether acetate or acetic acid hydroxyethyl ester; amides such as N-methylpyrrolidone; urea, tetramethyl urea and thiodiglycol. The emulsifiers can be anionic, cationic, non-ionic, amphoteric or zwitterionic.

Examples of surfactants include fatty alcohol sulphates, alkylsulphonates, alkylbenzene sulphonates, alklytrimethyl ammonium salts, alkylbetaine, α-olefin sulphonates, ethoxylated fatty alcohols, ethoxylated nonylphenols, fatty acid alkanolamides, ethoxylated esters of fatty acids, polyglycol ether sulphates of fatty acids and alkyl polyglucosides.

Examples of thickeners include higher fatty alcohols, starches, cellulose derivatives, vaseline, paraffin oil, fatty acids and other fatty components in emulsified form, water-soluble polymer thickeners, such as natural gums, guar gum, xanthan gum, carob flour, pectin, dextran, agar-agar, amylose, amylopectin, dextrin, synthetic clays or hydrocolloids, such as polyvinyl alcohol.

Examples of conditioning agents include lanolin derivatives, cholesterol, pantothenic acid, water-soluble cationic polymers, protein derivatives, provitamins, vitamins, plant extracts, sugar and betaine.

Examples of auxiliary agents are electrolytes, antioxidants, fatty acid amides, sequestering agents, film-forming agents and preservatives, and beeswax.

Examples of non-ionic and/or anionic surfactants or emulsifiers include fatty alcohol sulphates, in particular lauryl sulphate and sodium cocoyl sulphate; ethoxylated fatty alcohol sulphates, in particular sodium lauryl ether sulphates with 2 to 4 molecular units of ethylene oxide, ethoxylated esters of fatty acids, ethoxylated nonylphenols, ethoxylated fatty alcohols, alkylbenzene sulphonates or alkanolamides of fatty acids, in amounts preferably ranging from about 0.1 to 30% by weight, more preferably from 0.2 to 15% by weight.

Examples of cationic surfactants are quaternary ammonium compounds; ammonium halides such as alkyltrimethylammonium, dialkyldimethylammonium and trialkylmethylammonium chlorides. Specific examples are cetyltrimethylammonium chloride, behentrimonium chloride, stearyltrimethylammonium chloride, distearyldimethylammonium chloride, lauryldimethylammonium chloride, lauryldimethylbenzylammonium chloride, tricetylmethylammonium chloride and quaternised protein hydrolysates.

As well as non-ionic organic thickeners with properties similar to wax and to non-ionic surfactants, the compositions can include the usual cosmetic cationic resins.

Particularly preferred are Polyquaternium-6 (poly(dimethyl-diallylammonium chloride)), Polyquaternium-7 (diethyldiallylammonium chloride/acrylamide copolymer), Polyquaternium-10 (cationic cellulose), Polyquatemium-11 (diethyl sulphate of N,N-dimethylaminoethylmethacrylic acid/PVP copolymer), Polyquaternium-22, Polyquaternium-35 and Polyquaternium-37 (trimethylaminoethyl methacrylate chloride polymer), either alone or in mixtures thereof. The total amount of said cationic resins in the dye can range from about 0.1 to 6% by weight.

EXAMPLES

The ingredients listed in the examples are named according to the INCI nomenclature (European Community Decision 2006/257/EC as amended—International Nomenclature of Cosmetic Ingredients).

Table 1 shows an example of a composition according to the invention (F1*) and a comparative placebo formula (F2). A formulation F1A, similar to F1*but with pH 4, is also shown. The three formulations are used in the tests described below.

TABLE 1 leave-in spray pre-treatment

| INCI | F1* (pH 9) (% AMOUNT) | F2 (pH 9) (% AMOUNT) | F1A (pH 4.4) |
|---|---|---|---|
| AQUA (WATER) | q.s. | q.s. | q.s. |
| PROPANEDIOL | 3 | 5 | 3 |
| LEVULINIC ACID | 1.5 | — | 1.5 |
| TRISODIUM ETHYLENEDIAMINE DISUCCINATE | 0.945 | 2 | 0.945 |
| CETRIMONIUM CHLORIDE | 0.75 | 0.75 | 0.75 |
| SODIUM HYDROXIDE | 0.45 | 0.50 | — |
| GLYCOLIPIDS | 0.045 | 0.55 | 0.045 |

Table 2 shows the post-treatment formula according to the invention (F3*) and a comparative placebo formula (F4) used in the examples below.

TABLE 2 rinse-off post-treatment formula at pH 4.5

| INCI | F3* (% AMOUNT) | F4 (% AMOUNT) |
|---|---|---|
| ACQUA (WATER) | q.s. | q.s. |
| CETEARYL ALCOHOL | 5 | 5 |
| HYDROXYPROPYL STARCH PHOSPHATE | 5 | 3 |
| BEHENTRIMONIUM CHLORIDE | 2 | 2 |
| CITRIC ACID | 2 | 4 |
| STEREAMIDOPROPYLDIMETHYLAMINE | 2 | 2 |
| BIS-CETEARYL AMODIMETHICONE | 1.8 | 3 |
| BEHENTRIMONIUM METHOSULPHATE | 0.64 | 0.64 |
| ISOPROPYL ALCOHOL | 0.64 | 0.64 |
| PHENOXYETHANOL | 0.42 | 0.42 |
| SODIUM HYDROXIDE | 0.33 | 0.36 |
| ETHYLHEXYLGLYCERIN | 0.2 | 0.2 |
| DISODIUM EDTA | 0.15 | 0.30 |
| ZINC PCA | 0.1 | 0.5 |

Table 3 shows the formula of the bleaching powder used in the examples below.

TABLE 3

| bleaching powder | |
|---|---|
| INCI | F5 (% AMOUNT) |
| POTASSIUM PERSULPHATE | q.s. |
| SODIUM SILICATE | 20 |
| MAGNESIUM CARBONATE | 8 |
| SODIUM STEARATE | 5 |
| AMMONIUM PERSULPHATE | 5 |
| SODIUM METASILICATE | 3.5 |
| EDTA | 2 |
| HYDROXYETHYLCELLULOSE | 1.65 |
| PARAFFINIUM LIQUIDUM (MINERAL OIL) | 1.5 |
| XANTHAN GUM | 0.55 |
| POTASSIUM ALGINATE | 0.5 |
| SILICA | 0.48 |
| HYDROXYPROPYL GUAR HYDROXYPROPYLTRIMONIUM CHLORIDE | 0.3 |
| PARFUM (FRAGRANCE) | 0.25 |

Example 1

Differential Scanning Calorimetry (Dsc)

Differential scanning calorimetry is used to measure the enthalpy of keratin denaturation (delta HD), which is controlled by the integrity of the alpha-helix structure, and the keratin denaturation temperature (TD), which depends on the density of the crosslinking bonds in the cortex (Wortmann et al., J Cosmet. Sci. July-August 2002; 53(4):219-28; Wortmann et al., J Cosmet. Sci. July-August 2007; 58(4): 311-7).

Aggressive cosmetic treatments, which damage the hair bonds, cleave the chemical bonds in the hair, with a consequent reduction of TD. A repair treatment should restore the peak temperature to the level of natural virgin (untreated) hair, demonstrating its ability to restore the bond density in the cortex.

A METTLER TOLEDO STARE SYSTEM DSC 3 differential scanning calorimeter was used for this study. As the preliminary data and those reported in the literature demonstrate that bleaching treatment gives rise to a marked reduction in TD, it is possible to evaluate how "bond rebuilder" compositions can restore the bond density. The evaluation was conducted on five IHIP level 2 (dark brown) locks of human hair. One lock was left virgin, ie. untreated. Pre-treatment formula F1* according to the invention was applied to one lock, which was then bleached with formula F5; pre-treatment formula F2 (placebo) was applied to one lock, which was then bleached with formula F5; pre-treatment formula F1A was applied to one lock, which was then bleached with formula F5. One lock was bleached with formula F5 without any pre-treatment. One lock was subjected to the same bleaching treatment but adding Wella Wellaplex no. 1 Bond Maker (pH 9.30) to the mixture of bleaching powder and activator, according to the instructions for use. The bleaching treatment was conducted by mixing bleaching powder F5 with Alfaparf Milano Oxid'o 30 vol activator at the ratio of 1:2.

The mixture was applied to the locks and left to act for 40 minutes at 30° C. The locks were then rinsed, washed with a standard shampoo (containing 9.5% sodium laureth sulphate and 3% cocamidopropyl betaine) and blotted dry on paper. After drying with a dryer, the crucibles were prepared for analysis. Portions about 2 mm long were cut from the tips of the locks. About 6.0±0.5 mg of said pieces of locks was weighed in a stainless steel crucible together with 40 microlitres of water. The container was closed and left to stand for 24 hours to achieve a hydration balance in the fibres. The crucible was then inserted into the furnace of the instrument, and the analysis protocol was started, involving a heating ramp from 30 to 180° C., with a heating rate of 10° C./min. The measurement was repeated three times per lock. The data collected were processed with STARe software (Mettler Toledo).

Table 4 shows the mean value of TD measured from the three crucibles (MEAN), the delta of TD compared with the bleached hair (142.73° C., delta T), and the percentage difference relative to the delta T between virgin and bleached hair (10.86° C., % difference). FIG. 1 shows the mean denaturation temperatures TD measured from the various samples.

TABLE 4

| RESULTS OF DSC PRE-TREATMENT TEST | | | |
|---|---|---|---|
| Treatment | MEAN | delta T | % difference |
| Natural hair, level 2 | 153.59 | | |
| Bleached hair (reference ) | 142.73 | 10.86 | 0% |
| F2 Placebo pre-treatment | 143.21 | 0.48 | 4.4% |
| F1* Pre-treatment at pH 9 with levulinic acid | 146.65 | 3.92 | +36% |
| F1A Pre-treatment at pH 4 with levulinic acid | 145.51 | 2.78 | +25.6% |
| Wellaplex step 1 | 143.43 | 0.7 | 6.4% |

The data demonstrate that a bleaching treatment gives rise to a significant reduction in TD (−10.86° C.). Application of "placebo" formulation F2, not containing levulinic acid, gives rise to a modest recovery of TD. Application of pre-treatment F1* at pH 9 protects the hair by limiting bleaching damage. Application of pre-treatment F1A at pH 4.4 protects the hair to a lesser extent.

Conversely, the Wellaplex no. 1 Bond Maker treatment provides slight protection, comparable to that of placebo formula F2. These findings demonstrate that the slightly alkaline pre-treatment containing levulinic acid protects the bond density in the hair cortex.

A similar test was conducted by comparing the complete treatment according to the invention with the complete Wella treatment and the complete placebo treatment. The product Wellaplex no. 2 Bond Stabilizer was then applied to the bleached lock to which Wella Wellaplex no. 1 Bond Maker had been added, and processed according to the instructions for use. Post-treatment formula F3* was applied to the lock pre-treated with formula F1*, after bleaching. Post-treatment formula F4 was applied to the lock pre-treated with formula F2, after bleaching. Treatments F3* and F4 were left to act for 10 minutes and then rinsed. After drying with a dryer, the crucibles were prepared for analysis by the same procedure as specified above.

Table 5 shows the mean value of TD measured from the three crucibles (MEAN), the delta of TD compared with level 2 virgin hair (153.59° C., delta T), and the percentage difference compared with the delta T of bleached hair (10.86° C., % difference).

Figure 2:
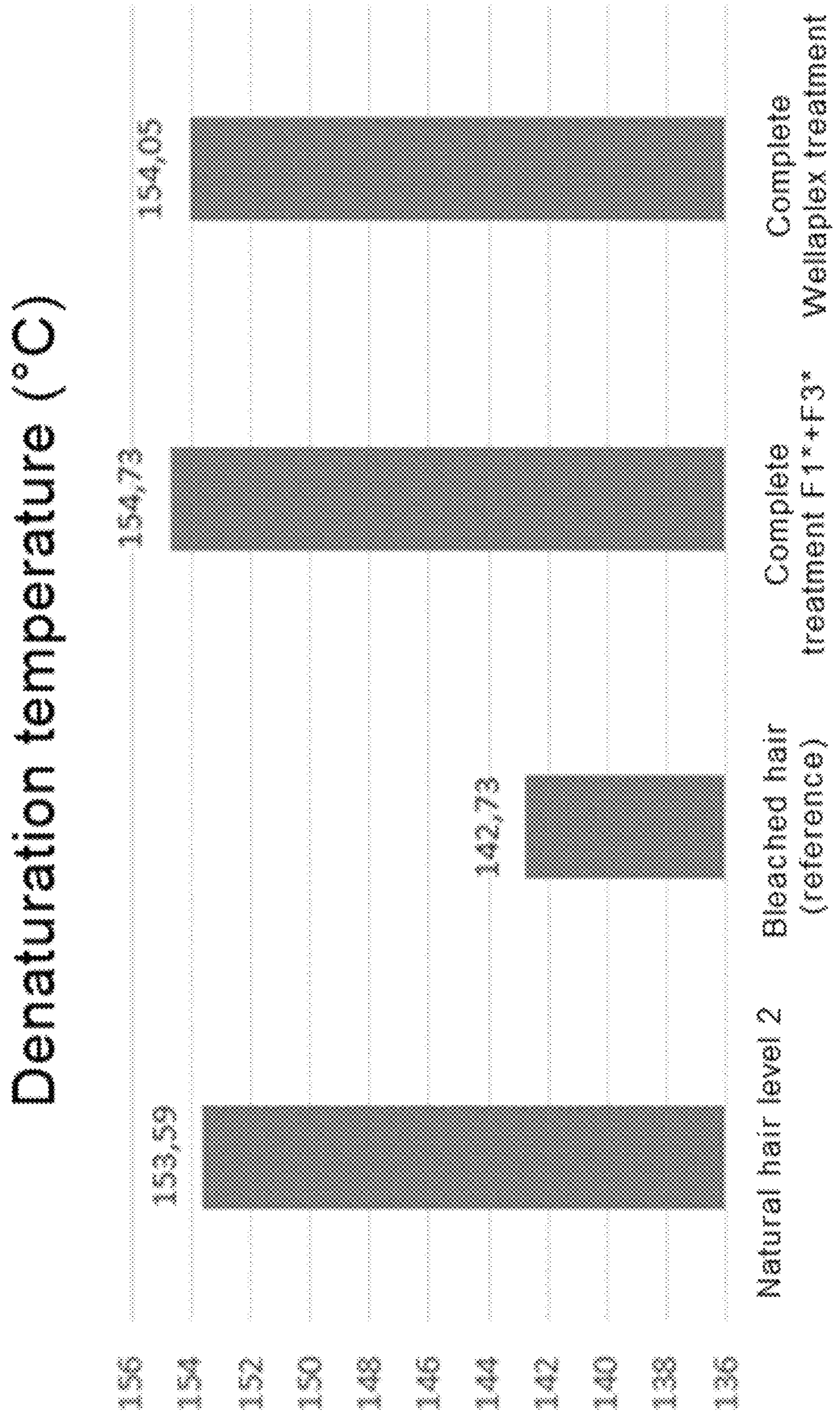
FIG. 2 shows the mean denaturation temperatures TD measured from the various samples.

The chart in FIG. 2 shows the mean denaturation temperatures TD measured from the various samples.

TABLE 5

| RESULTS OF DSC TEST ON COMPLETE TREATMENT | | | |
|---|---|---|---|
| Treatment | MEAN | delta T | % difference |
| Natural hair, level 2 | 153.59 | | |
| Bleached hair (reference ) | 142.73 | 10.86 | 0% |
| F1* pre-treatment + bleaching + F3* post-treatment | 154.73 | −1.14 | 110% |
| Wellaplex step 1 + bleaching + step 2 | 154.05 | −0.46 | 104% |

The application of complete treatment F1*+F3* according to the invention gives rise to a recovery of TD similar to that effected by the complete treatment with Wellaplex. However, the fact that the pre-treatment according to the invention performs better than Wellaplex step 1 means that the bond density is already protected during the bleaching/dyeing treatment, thereby providing the benefits demonstrated in the examples below.

Example 2

Tensile Strength Test

Figure 3:
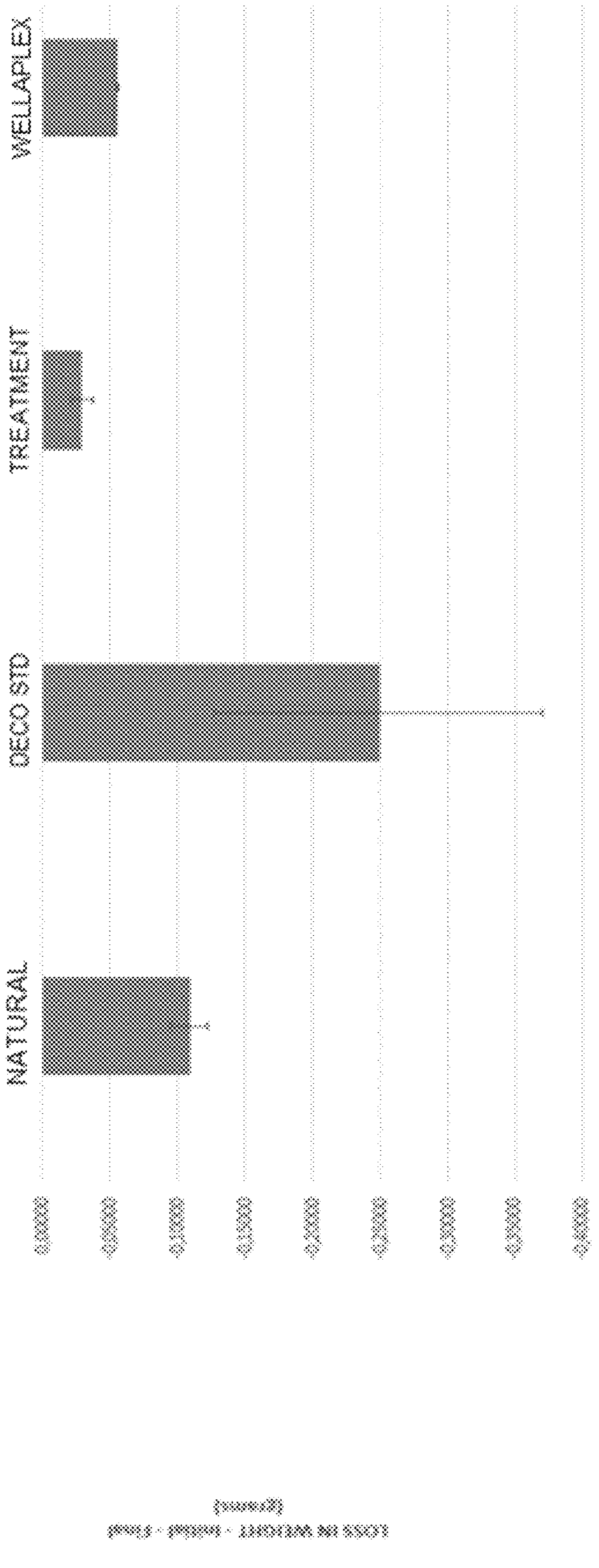
FIG. 3 shows the results of the tensile strength test.

The test involves subjecting the lock to repeated combing to evaluate the efficacy of various cosmetic treatments against damage caused to the hair by mechanical stress, such as brushing. The more the hair is weakened by prior chemical treatments such as bleaching, dyeing and permanent styling, the lower its resistance to mechanical stress will be. The locks are attached to a specific support and subjected to repeated combing for one hour by a multi-comb rotary system that moves at the speed of 85 rpm, giving a total of about 20,400 combing strokes/hour. The rotary system is equipped with 4 identical antistatic combs. The locks are weighed before and after the test, and the weight difference is calculated. The greater the weight loss, the greater the breakage of hair fibres. The results of this test are directly correlated with the degree of hair damage; the more badly damaged the hair, the greater the weight loss. Protective and/or restructuring cosmetic treatments give rise to a reduction in the number of hair fibre breakages, with a consequent reduction in weight loss. The test is conducted in an air-conditioned room with a temperature of 22-25° C. and 50-60% relative humidity. The evaluation was conducted on IHIP level 2 locks of human hair subjected to bleaching and treatments as described in the preceding example. The results are set out in Table 6 and FIG. 3.

TABLE 6

| RESULTS OF TENSILE STRENGTH TEST ON COMPLETE TREATMENT | | | | |
|---|---|---|---|---|
| Treatment | Starting weight | Final weight | Difference weight | % loss compared with natural hair |
| Natural hair, level 2 | 1.86069 | 1.75193 | 0.01412 | 0% |
| Bleached hair (reference) | 1.87403 | 1.62497 | 0.12175 | +129% |
| F1* pre-treatment + bleaching + F3* post-treatment | 1.90540 | 1.87610 | 0.00765 | −73% |
| Wellaplex step 1 + bleaching + step 2 | 1.87930 | 1.82410 | 0.00028 | −49% |

The treatment according to the invention reduces broken hair loss by 73%, as against 49% with the Wellaplex treatment.

Example 3

Colour Equalisation Test

The hair usually differs between the healthier root and the more damaged lengths/tips, which can adversely affect the colour result when it is dyed.

Hair equalisation means standardising the hair before the cosmetic dyeing/bleaching treatment so that the dyes/bleaching agents will be distributed evenly throughout the hair length, providing a homogeneous result. The colour equalisation test was conducted on IHIP level 10 (very light blonde) locks.

To simulate the irregularity of the hair from root to tip, 12 locks were bleached from mid-length to the ends, leaving the portion from root to mid-length in the natural state.

Bleaching was performed by using formula F5 mixed with the activator Alfaparf Milano Oxid'o 40 vol at the ratio of 1:2, applied to the locks and left to act for 35 minutes at 30° C. The locks were then rinsed, washed with standard shampoo and dried for 30 minutes at 55° C. in a dryer.

Pre-treatment F1* (0.5 g of product for each lock weighing about 2 g) was applied to 3 locks thus obtained, and left to act for 5 minutes at room temperature. Pre-treatment F2 (0.5 g of product for each lock weighing about 2 g) was applied to another 3 locks, and left to act for 5 minutes at room temperature. No pre-treatment was applied to another 3 locks.

The dye EOC CUBE 8.1, mixed with Alfaparf Milano Oxid'o 30 vol at the ratio of 1:1.5, was then applied to each lock, The dye was left on the locks for 35 minutes at a temperature of 30° C.

The locks were then rinsed and dried for 30 minutes at 55° C. in a dryer. The last three locks were subjected to the same dyeing treatment, but adding Wella Wellaplex no. 1 Bond Maker to the mixture of dye and activator according to the instructions for use.

The colouring result on the 12 locks was evaluated with a Konica Minolta colorimeter and processed with SpectraMagic NX software. In the CIELAB colour space, L* indicates sheen and a* and b* are the colour coordinates. a* and b* indicate the colour directions: +a* is the direction of red, −a* is the direction of green, +b* is the direction of yellow and −b* is the direction of blue. Differences in colour can be expressed by the ΔE values, which are defined by the following equation:

$$\Delta E=[(\Delta L^*)2+(\Delta a^*)2+(\Delta b^*)2]1/2$$

The lower the value of ΔE between the bleached portion of lock and the natural portion, the greater the equalisation. The recovery percentages are calculated as follows:

(ΔE between bleached portion of lock and natural portion after pre-treatment/ΔE between bleached portion of lock and natural portion with no pre-treatment)×100. Table 6 shows the mean values of ΔE for each set of 3 locks, and the recovery percentages obtained.

TABLE 7

| RESULT OF COLOUR EQUALISATION STUDY ON PRE-TREATMENT | L*(D65) | a*(D65) | b*(D65) | Eab | dE*ab (D65) | Difference in ΔE compared with comparator | % recovery |
|---|---|---|---|---|---|---|---|
| COMPARATOR without pre-treatment (normal hair) | 43.15 | 1.36 | 2.57 | 43.24 | | | |
| COMPARATOR without pre-treatment (bleached hair) | 36.88 | 1.42 | 0.27 | 36.91 | 6.68 | | |
| Placebo F2 (normal hair) | 39.36 | 1.39 | 1.9 | 39.43 | | | |
| Placebo F2 (bleached hair) | 34.02 | 1.35 | −0.69 | 34.05 | 5.94 | 0.74 | 11% |
| Pre-treatment F1* (normal hair) | 40.39 | 1.41 | 3.02 | 40.52 | | | |
| Pre-treatment F1* (bleached hair) | 36.63 | 1.50 | 0.39 | 36.66 | 4.59 | 2.09 | 31.3% |
| Pre-treatment F1A (normal hair) | 42.63 | 1.12 | 2.41 | 42.71 | | | |
| Pre-treatment F1A (bleached hair) | 36.67 | 1.39 | 0.18 | 36.69 | 6.37 | 0.31 | 4.6% |
| WELLA STEP 1 (normal hair) | 40.55 | 1.40 | 2.46 | 40.65 | | | |
| WELLA STEP 1 (bleached hair) | 34.36 | 1.32 | −0.38 | 34.39 | 6.81 | −0.13 | −1.9% |

The higher the percentage recovery, the better the colour equalisation/standardisation of the hair from root to tip compared with dyeing without pre-treatment.

The application of pre-treatment F1* according to the invention significantly improves colour equalisation (+31.3%), while treatment with Wellaplex no. 1 Bond Maker has no positive influence on equalisation, but slightly worsens it. The use of placebo pre-treatment F2 at pH 9 gives rise to a slight improvement in equalisation (+11%), but is still better than pre-treatment F1A at pH 4.4 (+4.6%), demonstrating that pre-treatment at an acid pH worsens the evenness of the colour.

Example 4

Resistance of Colour to Washing

The washing resistance test was conducted on IHIP level 10 (very light blonde) locks. 6 locks were subjected to a bleaching treatment to simulate the damage typical of hair tips, where greater colour fading is commonly observed after washing. Bleaching powder F5 was mixed with the activator Alfaparf Milano Oxid'o 40 vol at the ratio of 1:2, applied to the locks and left to act for 35 minutes at 30° C. The locks were then rinsed, washed with standard shampoo and dried for 30 minutes at 55° C. in a dryer. Formula F1* was applied to 3 locks and left to act for 5 minutes at room temperature. Formula F2 was applied to the other 3 locks and left to act for 5 minutes at room temperature.

The dye EOC CUBE 6.661, mixed with Alfaparf Milano Oxid'o 30 vol at the ratio of 1:1.5, was then applied to each lock. The dye was left to develop on the locks for 35 minutes at a temperature of 30° C.

The locks were then rinsed and dried for 30 minutes at 55° C. in a dryer. Post-treatment formula F3* was applied to the lock pre-treated with formula F1*. Post-treatment formula F4 was applied to the lock pre-treated with formula F2. Three other locks were subjected to the same dyeing and bleaching treatment, but adding Wella Wellaplex no. 1 Bond Maker to the mixture of bleach and activator, according to the Wellaplex instructions. The lock was then rinsed and blotted dry; the product Wellaplex no. 2 Bond Stabilizer, processed according to the instructions for use, was then applied.

A Konica Minolta colorimeter was used to evaluate the resistance of the colour to washing. The measurement was taken at time zero, and repeated after 3, 6, 9 and 12 washes with shampoo. Here again, the colour differences can be expressed by ΔE values. The lower the value of ΔE, the less the colour will fade after washing. Table 8 shows the ΔE data obtained after 12 washes.

TABLE 8

| Loss of colour after 12 washes with complete treatment | |
|---|---|
| Formula | ΔE |
| F1* + F3* | −12% |
| F2 + F4 | −23% |
| WELLA STEP 1 + STEP 2 | −19% |

The complete treatment with F1*+F3* pre- and post-treatments according to the invention improves the resistance of cosmetic colour to washing more than the complete treatment with Wellaplex.

Example 5

Frizz Effect Test

The frizz effect test was conducted on IHIP level 10 (very light blonde) locks. 6 locks were subjected to a bleaching treatment to simulate damaged hair. Bleaching powder F5 was mixed with the activator Alfaparf Milano Oxid'o 40 vol at the ratio of 1:2, applied to the locks and left to act for 35 minutes at 30° C. The locks were then rinsed, washed with standard shampoo and dried for 30 minutes at 55° C. in a dryer. Formula F1* was applied to 3 locks and left to act for 5 minutes at room temperature. Formula F2 was applied to the other 3 locks and left to act for 5 minutes at room temperature. The dye EOC CUBE 6.661, mixed with Alfaparf Milano Oxid'o 30 vol at the ratio of 1:1.5, was then applied to each lock.

The dye was left to develop on the locks for 35 minutes at a temperature of 30° C. The locks were then rinsed and dried for 30 minutes at 55° C. in a dryer. Post-treatment formula F3* was then applied to the 3 locks pre-treated with formula F1*. Post-treatment formula F4 was applied to the 3 locks pre-treated with formula F2. Three other locks were subjected to the same dyeing and bleaching treatment, but adding Wella Wellaplex no. 1 Bond Maker to the mixture of bleach and activator, according to the Wellaplex instructions. The lock was then rinsed and blotted dry; the product Wellaplex no. 2 Bond Stabilizer, processed according to the instructions for use, was then applied. To evaluate frizziness, the locks were hung on a Manfrotto 300 panoramic tripod to obtain images, standardising the exposure conditions.

The entire study was conducted in an air-conditioned room at a temperature of 22-25° C., with 50-60% relative humidity. The photos were taken with a Sony Alpha 5100 mirrorless camera.

The photos were then analysed with Image J (NIH) software and the images were processed with a pre-set macro, only displaying the fibres responsible for the frizz effect. The corresponding area was then quantified.

Table 9 shows the mean frizzy areas for each set of locks, and the difference compared with the untreated locks.

Figure 4:
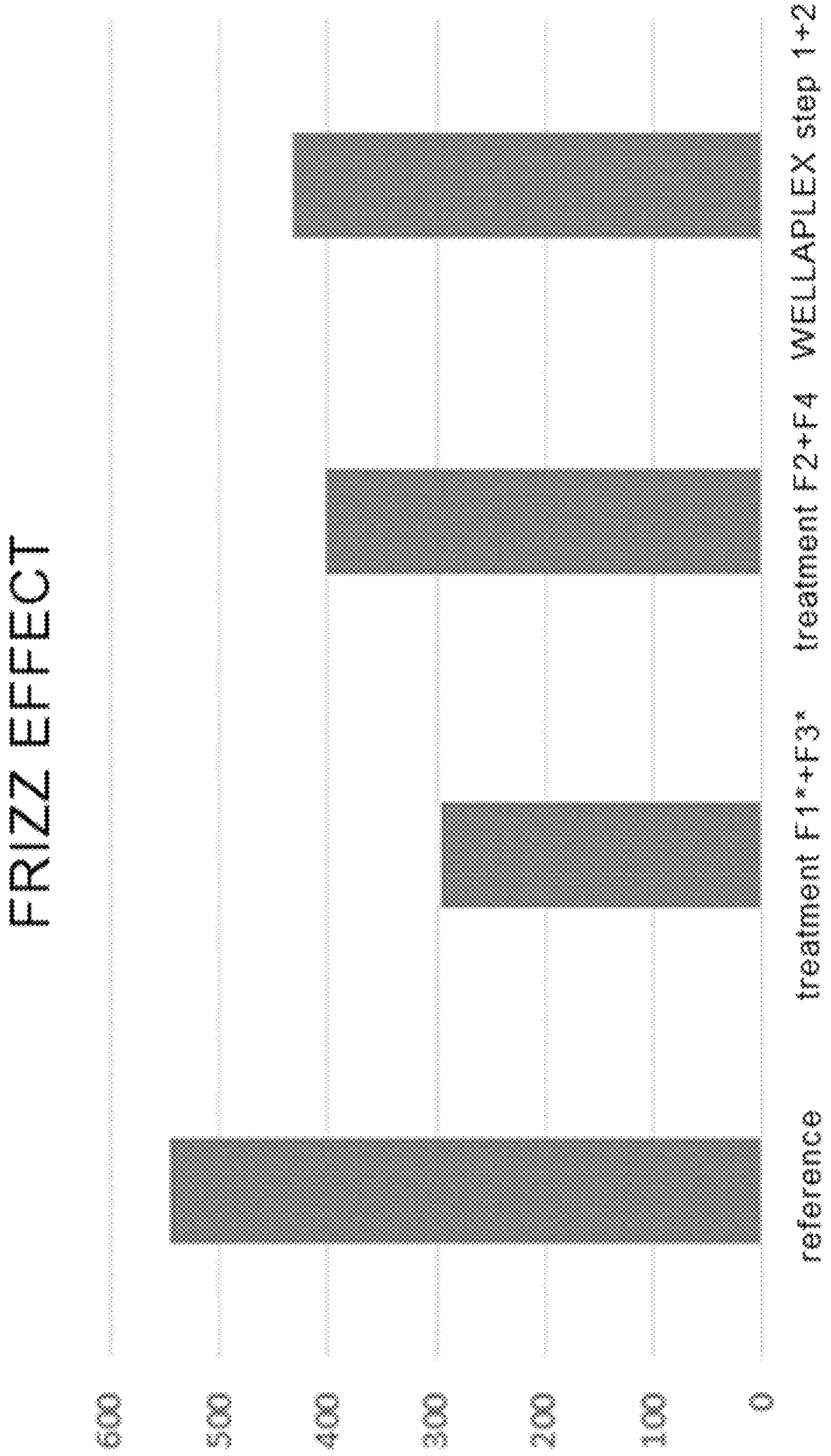
FIG. 4 shows the graphical representation of the mean frizzy areas for each set of locks and the difference compared with the untreated locks.

FIG. 4 contains the graphical representation of the data.

TABLE 9

RESULTS OF FRIZZ EFFECT TEST WITH COMPLETE TREATMENT

| Formula | Frizzy area (mm2) | SD | % difference |
|---|---|---|---|
| Comparator | 545 | 73.1 | |
| Treatment F1*+ F3* | 295 | 104.4 | −46% |
| Treatment F2 + F4 | 401 | 101.8 | −26% |
| WELLA STEP 1 + STEP 2 | 432 | 101.1 | −21% |

The data demonstrate that the lock subjected to pre- and post-treatment F1*+F3* according to the invention improves the frizz effect, and the hair is much more manageable than that subjected to the Wellaplex treatment.

The invention claimed is:

1. A method for protecting and restructuring hair, comprising applying to the hair, prior to a dyeing or bleaching treatment, a first composition at pH 7.0-9.5 comprising levulinic acid and a post-treatment, following the dyeing or bleaching, with a second composition at pH 3.5-4.5 comprising pyrrolidone carboxylic acid zinc salt.

2. A method according to claim 1 wherein the concentration of levulinic acid in the first composition is between 0.5 and 2.5% by weight.

3. A method according to claim 1 wherein the concentration of pyrrolidone carboxylic acid zinc salt in the second composition is between 0.01 and 0.5% by weight.

4. A kit comprising:

a first pre-treatment composition at pH 7.0-9.5 comprising levulinic acid at a concentration ranging between 0.5 and 2.5% by weight;

a second post-treatment composition at pH 3.5-4.5 comprising pyrrolidone carboxylic acid zinc salt.

5. A kit according to claim 4 wherein the first pre-treatment composition and the second post-treatment composition are in the form of an O/W (oil-in-water) or W/O (water-in-oil) emulsion, aqueous solution, biphasic liquid, gel, oil, aerosol or mousse, or in solid form.

6. A kit according to claim 4 wherein the first pre-treatment composition and the second post-treatment composition comprise one or more ingredients selected from solvents, emulsifiers, wetting agents, surfactants, thickeners, conditioners and auxiliaries.

7. A method for protecting and restructuring hair during a dyeing or bleaching treatment using the kit according to claim 4, said method comprising:

applying to the hair, prior to the dyeing or bleaching treatment, the first pre-treatment composition at pH 7.0-9.5, said first pre-treatment composition comprising levulinic acid at a concentration ranging between 0.5 and 2.5% by weight; and a post treatment, following the dyeing or bleaching treatment, with the second post-treatment composition at pH 3.5-4.5, said second post-treatment composition comprising pyrrolidone carboxylic acid zinc salt.

* * * * *